United States Patent [19]

Blank

[11] Patent Number: 5,134,205

[45] Date of Patent: Jul. 28, 1992

[54] CERTAIN HYDROXYALKYL CARBAMATE COMPOUNDS, HOMOPOLYMERS AND COPOLYMERS THEREOF AND USES THEREOF

[75] Inventor: Werner J. Blank, Wilton, Conn.

[73] Assignee: King Industries, Norwalk, Conn.

[21] Appl. No.: 329,758

[22] Filed: Mar. 28, 1989

Related U.S. Application Data

[62] Division of Ser. No. 20,431, Mar. 2, 1987, Pat. No. 4,820,830.

[51] Int. Cl.$^5$ .................... C08L 61/20; C07C 269/04
[52] U.S. Cl. .................................. 525/509; 525/419; 525/439; 525/452; 525/461; 560/158
[58] Field of Search ............... 525/509, 439, 419, 452, 525/461

[56] References Cited

U.S. PATENT DOCUMENTS

| | | | |
|---|---|---|---|
| 2,582,594 | 1/1952 | Kropa | 525/437 |
| 2,744,897 | 5/1956 | Drechsel . | |
| 2,802,022 | 8/1957 | Groszos . | |
| 3,950,285 | 4/1976 | Wolgemuth . | |
| 4,214,073 | 7/1980 | Passagne et al. . | |
| 4,268,684 | 5/1981 | Gugiolo . | |
| 4,431,795 | 2/1984 | Krimm et al. . | |
| 4,435,559 | 3/1984 | Valko . | |
| 4,484,994 | 11/1984 | Jacobs, III et al. | 525/504 |
| 4,501,874 | 2/1985 | Hanafin . | |
| 4,520,167 | 5/1985 | Blank et al. | 525/131 |
| 4,542,173 | 9/1985 | Schupp et al. . | |
| 4,588,783 | 5/1986 | Chang . | |
| 4,631,320 | 12/1986 | Parekh et al. . | |
| 4,705,885 | 11/1987 | Just et al. . | |
| 4,758,632 | 7/1988 | Parekh et al. | 528/383 |

FOREIGN PATENT DOCUMENTS

| | | |
|---|---|---|
| 0149156 | 7/1985 | European Pat. Off. . |
| 0196112 | 10/1986 | European Pat. Off. . |
| 3419744 | 11/1986 | German Democratic Rep. . |
| 3644370 | 7/1988 | German Democratic Rep. . |
| 3711947 | 10/1988 | German Democratic Rep. . |

OTHER PUBLICATIONS

Use of Urethane Glycols as Blocked Diisocyanates, V. V. Mikheev, N. V. Svetlakov, and L. V. Semenova, Lakokras, Mater. Ikh Primen. 1983, No. 6, 5–6
Behavior of Hydroxyurethanes ($\beta$-Hydroxyethyl Carbamates, L. Ya. Rappoport, et al. Zh. Org. Khim. 19, 1420–1423 (1983).
Thin-Layer Polycondensation (Literature Survey), A. S. Fomin, et al. Lakokras. Mater. Ikh Primen. 1983, No. 3, 20–22.

*Primary Examiner*—James J. Seidleck
*Assistant Examiner*—Vasu S. Jagannathan
*Attorney, Agent, or Firm*—Morgan & Finnegan

[57] ABSTRACT

This invention relates to certain polyamine hydroxyalkyl carbamate monomers, polymers and copolymers thereof and blends of the same with crosslinking film making agents and films thereof deposited on substrates.

9 Claims, No Drawings

CERTAIN HYDROXYALKYL CARBAMATE COMPOUNDS, HOMOPOLYMERS AND COPOLYMERS THEREOF AND USES THEREOF

CROSS REFERENCE TO RELATED APPLICATIONS

This application is a division of application Ser. No. 07/020,431 filed Mar. 2, 1987, now issued as U.S. Pat. No. 4,820,830.

BACKGROUND OF THE INVENTION

It is known that polyurethanes can be prepared from diols, polyester polyols, polyether polyols or other hydroxy functional compounds and/or di or polyisocyanates. This has been the most common route in the preparation of polyurethane polymers. The preparation of these polyurethanes from hydroxyalkyl carbamates has been described in the literature as will be identified hereinbelow. On the other hand, this invention relates to certain hydroxyalkyl carbamate compounds produced by reacting selected diamines with any one or more of the cyclic carbonates as defined hereinbelow. These carbamate compounds are prepared without the use of any isocyanate intermediates and can be used in the field of coating compositions preferably with a cross-linking agent such as aminotriazine compounds and resins produced therefrom such as melamine-formaldehyde reaction products and resins therefrom, urea-formaldehyde resins, epoxy resins, isocyanates or acrylic polymers containing reactive groups, such as hydroxyl groups, carboxyl groups, amide groups, amine groups and the like.

THE PRIOR ART

The instant applicant is aware of the following references: "The Preparation of Polymeric and Cyclic Urethanes and Ureas from Ethylene Carbonate and Amines" by Elizabeth Dyer and Harvey Scott, *JACS* (1956) pp 672-675 (U.S. Pat. No. 4,268,684). Additionally, the *Journal of Elastomers and Plastics*, Vol. 14, October, 1982, Pages 195-203. The U.S. Pat. No. 4,284,750 Amirsakis. Attention is directed to my copending application Ser. No. 896,260 filed Aug. 14, 1986 now abandoned. Additionally, see the U.S. Pat. Nos. 4,110,260 filed Aug. 14, 1986. Additionally, see the U.S. Pat. Nos. 4,110,667; 4,451,622; 4,419,407; 4,542,173; 4,533,704; 4,588,787; and 4,535,132. Each of these citations is incorporated herein by reference.

DESCRIPTION OF THE INVENTION

This invention relates to certain hydroxyalkyl carbamate compound and polymers, copolymers and interpolymers thereof. The carbamates are prepared by reacting certain cyclic carbonates with selected diamines. Each of these essential starting materials will be discussed in detail hereinbelow.

The cyclic carbonates used in the present invention may be represented as those having the structural formula:

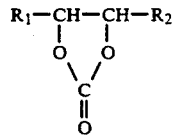

wherein $R_1$ or $R_2$ can be separately either Hydrogen or a $C_1$ to $C_{18}$ alkyl group or a phenyl group; $R_2$, alone, can also be $-CH_2-O-R_1$.

Suitable diamines that can be used for the preparation of the bicarbamates are the primary diamines having the following structural formula:

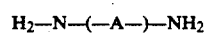

wherein A is a branched cycloalkylene group or a branched chain alkylene moiety having from 4 to 18 carbon atoms, said moiety having attached thereto at least one alkyl group. The preferred amines that are used in this invention are those wherein the distance between the amine groups is at least 4 or more carbon atoms and there is at least one methyl group substituent in the alkylene moiety. Illustrative of these preferred diamines are 2-methyl 1,5-pentane diamine; 2-ethyl 1,4-tetramethylene diamine; 2,2,4-trimethyl 1,6-hexane diamine; 2,4,4-trimethyl hexamethylene diamine; 3-aminomethyl-3,5,5-trimethylcyclohexylamine and the like.

A host of the carbonates are well known in the art and a substantial plurality of them are available commercially. As a consequence, repetitious recapitulation of these species would perhaps border on redundancy. It is deemed sufficient, therefore, to mention some of the better known carbonates such as ethylene carbonate, propylene carbonate, butylene carbonate, amylene carbonate and the like. These carbonates and other comparable carbonates may be used either singly or in combination with one another.

Among other parts of our invention, I have surprisingly found that the preparation of polyurethanes from bishydroxy-alkyl carbamate of 2-methyl 1,5-pentane diamine (MPDA) offers significant advantages versus the preparation from other hydroxyalkyl carbamates. The MPDA based polyurethanes are not crystallizing and precipitating out of solutions; polyurethanes can be prepared by transesterification. High levels of polyurethane linkages can be incorporated into the structure without loss of solubility. This enables the preparation of low molecular weight polyurethane polyols which do not crystallize; these polyols are useful in high solids coatings. These polyols are also useful in the preparation of flexible, abrasion-resistant and light-stable coatings for metal, wood, textile and paper substrates. In addition, they can be used for the preparation of thermoplastic polyurethanes, printing inks, and thermoset or thermoplastic adhesives.

It has long been known that polyurethanes can produce coatings, films, adhesives, inks and printing pastes with high flexibility, toughness and abrasion resistances.

The conventional procedure in the preparations of polyurethane polyols involves the preparation of a macro diol or polyol-based on a polyether or polyester resin and further chain extending this diol with a di or poly isocyanate to a polyester or polyether urethane dio or polyol. These functional polyols can be either thermoplastic polymers or they can be further cross-linked by a melamine resin, a polyisocyanate, or any other appropriate mechanism.

The present invention provides an improved process for the preparation of a polyurethane diol or polyol from a hydroxyalkyl carbamate and a diol or polyol or ester and the products thus produced.

One of the advantages of my process resides in the use of low or non-toxic precursors in the preparation of the polyurethanes. Still further, light stable polyurethanes based on aliphatic amines can be prepared. In addition, low molecular weight oligomeric polyurethanes can be prepared which do not crystallize or phase separate.

Suitable diols or polyols for the preparation of a polyurethane diol or polyol that can be used are the polyether diols or polyols derived from ethylene oxide and/or propylene oxide and higher-olefin oxides and/or tetrahydrofuran. These polyols can be tri or higher functional. The di and trifunctional polyols are preferred. These higher functional polyols may lead to gelation during the preparation of the polyurethane polyol and, for this reason, may be avoided.

The number average degree of polymerization of these polyols can be from several repeating polyether units such as 3 or 5 units up to about 40 or 50 units or more. Generally, a number average molecular weight of from about 200 to 1000 is preferred. However, number average molecular weights s low as about 150 and as high as about 5000 can be tolerated.

The polyesters suitable for my invention can be prepared from selected or suitable diols, triols or tetrols and an aromatic or aliphatic di- or tricarboxylic acid, or it can also be based on a hydroxyalkyl carboxylic acid or a lactone.

Among the diols that can be used are ethylene glycol, propylene glycol, 1,3-butyleneglycol, 1,4-butyleneglycol, neopentylglycol, diethyleneglycol, dipropyleneglycol, cyclohexane dimethanol, 1,6 hexanediol and the like. These diols may be used either singly or in combination with one another.

Suitable triols and tetrols that can be used are trimethylol propane, trimethylol ethane, glycerine, pentaerythritol, and the like. As before, these triols and tetrols may be used either singly or in combination with one another. The polyesters suitable for use in the present invention can be prepared by esterifying any one or more of the above listed polyhydric alcohols with an aliphatic, including cycloaliphatic polycarboxylic acid or aromatic di or tri-carboxylic acids (sometimes referred to as carboxylic acids free of non-benzenoid unsaturation). One can also use selected hydroxyalkylcarboxylic acids or a lactone such as caprolactone. Among the suitable polycarboxylic acids that can be used to make these polyestes, include malonic, succinic, glutaric, adipic, pimelic, suberic, azelaic and the like, and mixtures thereof.

Still further, one may use the alkyl esters and particularly the lower alkyl esters of any of these acids so as to provide a basis for a transesterification reaction. It is preferred to use the methyl esters of these acids principally for cost factors but other lower alkyl esters can be used such as the ethyl, propyl, butyl esters and the like. Some mixtures of methyl esters are available commercially and these mixtures are therefore additionally preferred for this reason. These commercially available mixtures of the methyl esters (DBE) have a mole ratio of about 0.5:1.5:0.6 dimethyl adipate, dimethyl glutarate and dimethyl succinate, respectively. Variations of this mole ratio can be tolerated depending on the desired properties of the final polyester resin. Lower viscosities are obtainable with higher levels of glutarate, for example. In addition, $C_{36}$ dimeric fatty acids are suitable for use in the preparation of these polyesters. The acids, (free of non-benzenoid unsaturation), that can be used are the aromatic polycarboxylic acids such as o-, m-, p-phthalic acid, trimellitic anhydride and the like. One can use the ethylenically unsaturated aliphatic acids such as maleic, fumaric, aconitic, itaconic acids or other anhydrides when available can be used singly or in combination with one another but generally in limited amounts. The polyesters used with the hydroxyalkyl carbamate compound or polymers thereof may have a number average molecular weight which varies between about 300 and about 2,500.

In order to prepare the polyurethanes of the present invention, a catalyst can be used such as certain tin com-pounds including the dibutyl tin dilaurate or alkoxide, or the zinc or lead salts or titanates. These catalysts may be used in the usual catalytic quantities, such as from about 0.005 to 1% by weight of the reactants and preferably 0.01 to 0.5% same basis.

A higher molecular weight polyester can be reacted with the hydroxyalkylcarbamates of the present invention without the removal of any reaction products, depending on the desired polyurethane. The resulting polymer incorporates the urethane linkage due to transesterification of the polyester and the carbamate. It is also possible to achieve coreaction between the polyester or polyether by transesterification of the urethane groups by removing the resulting glycol. Depending on reaction conditions, one may use a temperature of between about 120° C. and 200° C. and preferably between about 140° C. and 160° C. for the transesterification. The time cycle can be varied between 30 minutes and 8 hours, depending on temperature and catalyst used.

Polyester urethanes of the present invention can also be prepared from the monomeric diol or triol, the hydroxyalkylcarbamate and the diester of a di or polycarboxylic acid. One should, however, avoid the direct esterification with a carboxylic acid since it may lead to the hydrolysis of the carbamate.

The amount of urethane linkages employed in a polymer will depend on the properties desired. High levels of urethane linkages will result in polymers with increased hardness but with poorer solvent solubility. Therefore, it is generally desirable, in order to achieve a preferred balance of good properties, to have on the average at least one urethane group per molecule. The weight average molecular weight of the polyester urethane or polyester urethane should be controlled between about 400 and about 10,000. Preferably one should control said weight average molecular weight between about 1000 and about 5000. If so desired, in order to achieve unusual properties, some of the urethane groups in the polyurethane can also be derived from a di-isocyanate or a polyisocyanate.

In preparing the hydroxyalkylcarbamate of the present invention, one can generally use equal molar amounts of amines and cyclic carbonates or a slight excess of carbonate usign temperatures between room temperature (25° C.) and about 150° C. and preferably between about 50° C. and 120° C. for several hours or days until the reaction is complete.

The reaction time more explicitly will vary, of course, with the temperature, between 30 minutes and 8 hours but preferably between about 4 hours and 5 hours. In the preparation for these carbamates, when water is present, the stripping of the water will generally take about 2 hours to remove the water and to reduce the amine content to a level of about <0.5% by weight of the reaction mixture and until substantially all of the carbonate is removed.

In the stripping step, in the removal of the water and excess propylene carbonate, when present, from the carbamate, one may use a temperature of from about 100° C. and 225° C. at an absolute pressure of from about 0.05 to 200 torr for a period of time from about 10 seconds to 60 minutes. Preferably, one could use a temperature from about 120° C. and 150° C., at an absolute pressure of from about 0.1 to 150 torr, for a period of time from about 20 seconds to about 20 minutes. The properties of the hydroxyalkyl carbamates of the present invention are dependent on starting materials from a water white to slightly yellow to viscous liquid. The viscosity due to hydrogen bonding is usually high at room temperature. Depending on the molecular weight or the content of hydrophobic groups, the hydroxylalkyl carbamates are either water or organic solvent soluble. Most of these are soluble in a solvent with a solubility parameter of about 10 to 15.

In addition, the hydroxyalkyl carbamates are compatible without coreaction with most polyester polyether and acrylic resins used in coatings. In addition, a large range of amino resins such as the melamine, benzoguanamine, urea, glydoluril and also phenolaldehyde resins can be used as cross-linkers for the urethane polyester diols or hydroxyalkyl carbamates.

Although one of the principal uses of the carbamates of the present invention and the blends thereof with polyesters, polyether polyols and polyurethanes is in coating compositions, one may use these carbamates and blends thereof in such areas as adhesives, foams, moldings, elastomers, rim and laminates with whatever modifications may be required and with such additives as fillers, layers such as paper and the like.

In order that the concept of the present invention may be more fully understood, the following examples are set forth in which all parts are parts by weight unless otherwise indicated. These examples are set forth primarily for illustration and any specific enumeration of detail set forth therein should not be interpreted as a limitation on the case except as is indicated in the appended claims.

EXAMPLE 1

The preparation of 2-Methyl 1,5 pentanediamine bishy-droxyalkylcarbamates by reacting MPDA with a cyclic carbonate.

Into a suitable reaction vessel equipped with stirrer, thermometer, reflux condenser, inert-gas inlet and outlet tubes, there is introduced 116 parts (1 mol) of 2-methyl 1,5 pentanediamine (MPDA) is charged with agitation and heating. The reactor is blanketed with nitrogen. The low viscous solution is heated to 50° C., and slowly 224 parts (2.2 mols) of propylene carbonate is fed into the reactor. The reactions is very exothermic, and cooling is used to keep the reactor content between 90°-100° C. The addition time for the propy-lene carbonate is about 1-3 hours, depending on the rate of cooling.

After 4 hours, holding the reactor at 90°-100° C., the mixture is checked for amine content by acid titration. At that point, the free amine content should be below 1% of the reaction mixture. Holding for another 5 hours reduces the free amine level to <0.5%.

Product Characteristics

Solids content (60', 110° C.): 97.3%
Viscosity Brookfield, Pas: 1420
Residual amine content: 0.8 MEQ/g OR 0.92 g Amine/100 g
Solvent: Propylene carbonate For most applications the product can be used as is. Suitable products can be prepared with less excess of propylene carbonate if the reaction time is extended or the reaction temperature is increased. However, significantly higher temperatures can lead to the formation of ureas from the reaction of carbamates with free amines which can be undesirable.

EXAMPLE 2

Into a suitable reaction vessel, equipped as in Example 1, 10 mol of cyclohexane dimethanol (1442 parts), 9 mol of DBE, a dimethyl ester of a dibasic acid blend (16% dimethyl adipate, 61% dimethylglutarate, 23% dimethyl succinate) (1413 parts) are charged. The reaction mixture is heated under a blanket of gas to 120° C., and 1.0 part of a tin transesterification catalyst (Fascat 4201, M&T Chemical) is added. Then reaction is slowly heated to 200° C. and about 573 parts of methanol are removed from the reaction mix.

The reaction is completed by holding the system for 3 hours at 26" vacuum to remove any remaining methanol.

The calculated molecular weight of the polyester diol formed is about 2300 and the hydroxyl number, 49.

To this polyester, 340 parts of the reaction product Example 1 are added (1 mol), and the reaction mixture is heated to 160° C. and held there for 4 hours. The reaction mixture is then diluted with about 660 parts of methoxypropylacetate solvent.

Product Characteristics

Solids, 60', 110° C., %: 81.4
Viscosity Brookfield in cps: 4010
Appearance: Pale yellow, viscous liquid
MW Calc: 1200
OH Number: 96

EXAMPLE 3

To a suitable reactor 16 mol of 1,6-hexanediol (1890 parts), 15 mol of DBE, the dimethylester of a mixture of dibasic acids (2355 parts), and 2.0 parts of a tin catalyst (Fascat 4201, M&T Chemical) are charged. The reaction mix-ture is heated to 200° C. under nitrogen and removal of methanol. After most of the methanol has been removed, vacuum is applied, and the residual methanol is removed. (Total methanol collected 960 parts).

To this polyester, 680 parts of the reaction product of Example 1 are added and the reaction is continued at 160° C. for 5 hours.

After dilution with 500 parts of methoxypropylacetate solvent, the product has a solids content of 82.0 (60', 110° C.) and a viscosity of 1090 cps at room temperature. The color of the product is slightly yellow.

EXAMPLE 4

102 parts by weight of neopentanediamine are charged into a suitable reaction vessel equipped as before. To this amine, slowly are added 224 parts by weight of propylenecar-bonate. Cooling is used to keep the reaction below 100° C. The reaction mixture is kept 24 hours at 100° C. The amine content should drop to 0.2 milliequivalent (MEQ) of amine per gram. The temperature is then raised to 130° C. and the reaction is continued for 10 hours until the MEQ of amine drops to below 0.05/gram. The final product is of slight pale yellow color and has a solids content of 93.3% (60 min at 110° C.). The viscosity at room temperature is too high to measure.

EXAMPLE 5

To 137 parts of a commercially available blend of 2,2,4 trimethyl hexamethylene diamine and 2,4,4-trimethyl hexamethylene diamine, 224 parts of propylene carbonate are slowly added. The reaction temperature is cooled and then is held at about 100°–110° C. for about 10 hours.

The final product is a bishydroxypropyl carbamate of the diamine. The viscosity is 72100 cps at room temperature, and the solids content is 94.7% (60 min. at 110° C.) The final product has a residual amine content of 0.0672 MEQ/g.

EXAMPLE 6

There are charged into a suitable reactor 690 parts by weight of the 2-methylpentane diamine propylene carbonate reaction product of example 1 and 0.1 parts by weight of a tin transesterification catalyst (Fascat 4201 M&T Chemical). The blend is heated under nitrogen to 135°–145° C. and full vacuum is slowly applied. The distillate from the reaction is collected. The reaction is conducted for about 6 hours or until 105 parts by weight of distillate have been collected. The analysis of the distillate shows it to be predominantly propylene glycol and small amounts of unreacted propylene carbonate from the starting carbamate. The resulting polyurethane has a molecular weight of about twice that of the starting material and it is soluble in methoxypropylacetate solvent. About 100 parts by weight of methoxypropylacetate are added to the polyurethane resin. The resulting resin solution has a viscosity of 166,000 cps and a solids of 85.0%.

EXAMPLE 7

Comparative Example 489 parts by weight of a hydroxypropylcarbamate of ethanolamine (reaction product of 1 mol ethanolamine with 1 mol of propylene carbonate) are reacted with 157 parts by weight of DBE. 1.67 parts by weight of a tine catalyst are used.

The reaction is conducted at temperatures of 165°–193° C. A very dark colored product is obtained. The indications are that a cyclic carbamate was produced and no polymer.

EXAMPLE 8

Comparative Example 177 parts by weight of a hydroxypropyl carbamate of monoisopropanolamine, 157 parts by weight DBE, and 0.42 part of a tin transesterification catalyst are heated to 160°–165° C. Although methanol is collected, the product produced is predominantly a non-polymeric, very odoriferous cyclic carbamate.

EXAMPLE 9

Into a suitable reaction vessel equipped as before, a polyester is prepared by reacting 433 part by weight of cyclohexane dimethanol and 424 parts of DBE. A tin catalyst is used. The reaction is conducted as in Example 2. The final polyester is called to 160° C. and 92 parts of reaction product of example 4 are added. The reaction is carried out at 160° C. for 3 hours. The polymer melt is cooled to 80° C. and 200 parts of methoxypropyl acetate solvent are added.

EXAMPLE 10

Into a suitable reaction vessel equipped as before, 1146 parts by weight of neopentylglycol, 1570 parts by weight of DBE and 0.25 part of Fascat 4201 (M&T Chemical) are charged and heated under a nitrogen blanket to 200° C. The reaction methanol is collected. After about 450 parts of methanol have been collected, vacuum is slowly applied and the reaction is continued for an additional 3–5 hours until all 640 parts of methanol have been collected.

This polyester has a viscosity of 28900 cps. at 25° C. and a solids content of 99.3% (60 min. 110° C.). This polyester is used in the subsequent reactions.

EXAMPLE 11

691 parts by weight of polyester of example 10 is charged to a suitable reactor and heated to 160° C. under a nitrogen blanket. To this polymer, 255 parts by weight of the carbamate of example 5 are added. The reaction mixture is held at 160° C. for 6 hours, then cooled and diluted with 50 parts of xylene.

The final product has a viscosity of 7010 cps. at 25° C. and a solids content of 90.0% (60 min. 110° C.).

EXAMPLE 12

170 parts of isophoronediamine are placed into a reactor equipped with cooling and agitation. To the amine, 224 parts by weight of propylene carbonate are added over a 2 hour time period. The reaction is exothermic and the mixture is kept below 90° C. After 8 hours at 90° C., the remaining amine is determined by titration. The MEW/gram of product is 0.3. The reaction is continued at 100°–120° C. until the MEQ drops to below 0.15. The final product has a solids content of 96.4% (60 min. at 100° C.). The room temperature viscosity is too high to measure.

EXAMPLE 13

691 parts by weight of polyester of example 10 is charged to a suitable reactor and heated to 160° C. under a nitrogen blanket. To this polymer, 394 parts by weight of the carbamate of example 12 are added. The reaction mixture is held at 160° C. for 6 hours, then cooled and diluted with 50 parts of xylene. The final product has a viscosity of 6650 cps. at 25° C. and a solids content of 98.0% (60 min. 110° C.).

EXAMPLE 14

A commercially available high solids acrylic resin is separately blended with the polyols from Example 11 and Example 13 and a commercial grade of hexakismethoxymethylmela-mine (HMMM) are added. The formulation is catalyzed with a dodecylbenzenesulfonic acid diisopropanol amine salt. The quantities of ingredients are shown in the table. Xylene and MIBK are used as solvents. The coating formulation is coated onto iron phosphated steel panels (Bonderite 1000 treatment). The coating is cured at 120° C. and 150° C. respectively.

TABLE I

| | EXAMPLE 11 | | EXAMPLE 13 | |
|---|---|---|---|---|
| POLYOL # | | POLYOL # | | |
| OH NUMBER | 120.00 | OH NUMBER | 106.00 | |
| SOLIDS | 0.90 | SOLIDS | 0.98 | |
| | WEIGHT % CALC | | WEIGHT % CALC | |
| ACRYLIC | 54.78 | | 55.27 | |
| POLYOL | 23.48 | | 23.69 | |
| HMMM | 21.24 | | 20.54 | |
| CATALYST | 0.50 | | 0.50 | |
| TOTAL | 100.00 | | 100.00 | |
| SOLIDS % CALC | 58.60 | | 59.20 | |
| VISCOSITY cps | | 290.00 | | 325.00 |
| BONDER 1000 CRS | | | | |
| CURE SCHEDULE | 20 min. 120° C. | 150 | 20 min. 120° C. | 150 |
| FILM TH. MIL | .85–.95 | .85–.95 | .85–.95 | .85–.95 |
| HARDN. PENCIL | HB-F | H-2H | HB-F | F-H |
| KNOOP HARDNESS | 6.0 | 10.3 | 7.5 | 9.9 |
| IMPACT REVERSE IN. LB. | 140–150 | 5–10 | >160 | 5–10 |
| FRONT IN. LB. | 140–150 | 40–50 | 150–160 | 50–60 |
| CROSS HATCH ADHESION % | 40 | 50 | 95 | 50 |

EXAMPLE 15

To a commercially available acrylic resin solution, polyol and HMMM cross-linker are added and a 25% solution of a dodecylbenzene sulfonic acid diisopropanol amine salt (catalyst). The composition is applied on iron phosphated cold rolled steel panels and cured at 120° C. and 150° C. respectively.

EXAMPLE 16

Comparative, Formulation Without Polyurethane Polycol

The formulation is prepared as before only the polyol is omitted. The level of melamine cross-linker is adjusted based on the change in functionality of the formulation.

TABLE II

| | EXAMPLE 2 | | EXAMPLE 1 | |
|---|---|---|---|---|
| POLYOL # | | POLYOL # | | |
| OH NUMBER | 160.00 | OH NUMBER | 350.00 | |
| SOLIDS % | 98 | SOLIDS | 97.0 | |
| | WEIGHT % CALC | AS IS Charge | WEIGHT % CALC | AS IS Charge |
| ACRYLIC 75% | 53.43 | 93.33 | 47.83 | 93.33 |
| POLYOL | 22.90 | 30.77 | 20.50 | 30.83 |
| HMMM | 23.17 | 30.98 | 31.17 | 46.56 |
| CATALYST 25% | 0.50 | 2.61 | 0.50 | 2.91 |
| n-BUTANOL | | 10.00 | | 10.00 |
| XYLENE | | 20.00 | | 20.00 |
| TOTAL | 100.00 | 187.69 | 100.00 | 203.63 |
| SOLIDS % CALC | | 69.80 | | 71.87 |
| VISCOSITY cps | | 500.00 | | 832.00 |
| BONDER 1000 CRS | | | | |
| CURE SCHEDULE | 20 min 120° C. | 150° C. | 20 min 120° C. | 150° C. |
| FILM TH. MIL | 0.8–0.9 | 0.8–0.9 | 0.8–0.9 | 0.8–0.9 |
| HARDN. PENCIL | HB-F | H-2H | F-H | 2H-3H |
| KNOOP HARDNESS | 7.0 | 10.5 | 13.0 | 16.6 |
| IMPACT REVERSE IN. LB | >160 | 20–30 | 70–80 | 0–5 |
| FRONT IN. LB | >160 | 60–70 | 100–110 | 20–30 |
| CLEVLND HUMID. 43° C. 250 HRS | B-HB, 10 | F-H, 10 | F-H, 10 | 2H-3H, 10 |
| CROSS HATCH ADHESION | 90 | 90 | 100 | 15 |

As seen, the polyol contributes significantly to the flexibility of the coating. Using commercial available polyester polyol flexibilizer, the flexibility indeed improves but at a sacrific in adesin. The flexibility of the polyester urethane is also superior to the polyester.

TABLE III

| | Charge as is | |
|---|---|---|
| ACRYLIC 75% solution | 133.33 | 93.3 |
| HMMM | 25.51 | 37.9 |
| Catalyst 25% | 2.50 | 2.74 |
| Polyester polyol 98% | — | 30.9 |
| n-BUTANOL | 60.00 | 60.00 |
| TOTAL | 221.34 | 225.95 |
| SOLIDS 60' 110° C. | 54.58 | 61.0 |
| VISC. CPS | 190 | 305 |
| RESULTS | | |
| BONDER 1000 CRS | | |

TABLE III-continued

| | Charge as is | | | |
|---|---|---|---|---|
| CURE SCHEDULE | 20 min. 120° C. | 150° C. | 20 min. 120° C. | 150° C. |
| FILM TH. MIL | 0.75 | .75 | .85 | .85 |
| HARDN. PENCIL | F-H | H-2H | HB-F | H-2H |
| IMPACT REVERSE IN. LB | 20-30 | 0-5 | 40-50 | 5-10 |
| FRONT IN. LB | 30-40 | 10-20 | 60-70 | 60-70 |
| CROSS HATCH ADHESION % | 100 | 25 | 0 | 10 |

EXAMPLE 17
Comparative

Example 2 is repeated in all details, but he hydroxypropy carbamate of 2-methyl 1,5-pentanediamine is replaced with the bis carbamate of 1,6-hexaediamine. The resulting polyester urethane is not soluable in the methoxypropylacetate solvent and crystallizes on cooling and standing for several hours. Coatings prepared with this composition do not remain uniform and low gloss is observed presumably due to crystallization.

EXAMPLE 18

The addition of a polyester urethane polyol to a room temperature curing acrylic resin cross-linked with an isocyanate is explored. A commercially available acrylic resin, Acryloid AU608S (Rohm & Haas) is cross-linked with a aliphatic isocyantate Desmodure N-339 (Mobay). The formula-tion is catalysed with dibutyltin dilaurate (DBTL) and Ca-octoate. The polyurethane polyester modified formulation show significant improvement in flexibility versus the unmodified acrylic.

abrasion resistant and has a Knoop hardness of 15. The coating is resistant to methylethylketone rubs.

EXAMPLE 20

To 70 parts by weight of the polyurethane polymer of example 6, 37.5 parts of an 80% solution of a polymeric methoxymethylmelamine resin in isobutanol and 1 part of an alkylphosphate catalyst are added and the blend is diluted with 25 parts of 2-methoxy 1-propanol to application viscosity. The solution is applied on aluminum substrate and cured for 10 min at 150° C. The resulting film is scratch resistant and has excellent flexibility.

EXAMPLE 21

To 493 parts by weight of the urethane diol of example 1, 264 parts by weight of maleic anhydride and 100 parts by weight of xylene are added. The mixture is heated to 80° C. slowly. At 80° C. a slight exothermic reaction is seen. The reaction mixture is kept at 80° C. for 3 hours. The acid number of the reaction product is 184, calculated acid number is 208. Viscosity is 27600 cps at 25° C., the solids content is 86° 3% (60 min at 110° C.).

TABLE IV

| | FUNCTION MOL | GRAM SOLIDS | CHARGE AS IS | FUNCTION MOL | GRAM SOLIDS | CHARGE AS IS |
|---|---|---|---|---|---|---|
| Acrylic A0608S | 1 | 599.988 | 122.64 | 0.7 | 419.992 | 86.38 |
| Example 2 | 0 | 0.000 | 0.00 | 0.3 | 175.000 | 26.53 |
| Desmodure N-3390 | 1 | 215.385 | 29.35 | 1 | 215.385 | 20.67 |
| | | | 15.00 | | | 15.00 |
| DBTL 1% IN MIBK | | | 5.0000 | | | 5.0000 |
| Ca OCTOATE 5% | | | 0.50 | | | 0.46 |
| Total | 2.00 | 815.373 | 172.49 | 2.00 | 810.376 | 154.04 |
| Solids % calc. | | | 58.267 | | | 60.070 |
| Viscosity cps. | | | 659 | | | 705 |
| CURE TEMP | | | 25° C. | | | 25° C. |
| Time 24 hours knoop/MEK | | | 2./75 | | | 1.7/100+ |
| Time 168 hours knoop/MEK | | | 8.5/100+ | | | 8.3/100+ |
| Reverse impact in. lbs | | | 30-40 | | | >160 |
| FILM THICK Mil | | | .9-1.0 | | | .9-1.0 |
| BONDER 1000 CRS | | | | | | |
| CURE TEMP | | | 20 min 100° C. | | | 20 min 100° C. |
| HOURS AGED hours | | | 0    168 | | | 0    168 |
| FILM THICK mil | | | .9-1.0 | | | .9-1.0    .9-1.0 |
| HARDN. KNOOP/PENCIL | | | 16.5/H-2H    16.7/H-2H | | | 14.1/H-2H    16.3/H-2H |
| MEK RUBS | | | 100+    100+ | | | 100+    100+ |
| IMPACT REV in. lbs | | | 0-5    0-5 | | | >160    >160 |
| DIRECT in. lbs | | | 40-50    50-60 | | | >160    >160 |

EXAMPLE 19

To 60 parts by weight of the urethane diol of example 1, 40 parts by weight of hexamethoxymethylmelamine resin and 4 parts of dodecylbenzene sulfonic acid are added. The mixture has a solids content of 87.9% and a viscosity of 1000 cps. Film are applied at a wet film thickness of 1.5 mil on a plastic substrate and cured for 60 min at 65° C. The resulting film is water resistant,

EXAMPLE 22

To a commercially available high solids acrylic resin, the polyol of example 21 is added and the amounts of hexakismethoxymethylmelamine (HMMM) shown in the Table V. As a catalyst a 25% dodecylbenzene sulfonic acid solution 100% neutralized with diisopropanol amine is used. The coating is applied on iron phosphated cold rolled steel panels and cured. Excellent adhesion and cure is obtained at 100° C.

TABLE V

WEIGHT %

TABLE V-continued

|  | INPUT | CALC | AS IS |
|---|---|---|---|
| ACRYLIC | 70.00 | 52.19 | 93.33 |
| POLYOL EX 21 | 30.00 | 22.37 | 33.86 |
| HMMM | 34.13 | 25.45 | 34.83 |
| Catalyst | 0.00 | 0.00 | 0.00 |
| XYLENE |  |  | 40.00 |
| METHANOL |  |  | 20.00 |
| L-1980 |  |  | 1.00 |
| TOTAL | 134.13 | 100.00 | 223.02 |
| RESULTS |  |  |  |
| SOLIDS % CALC |  | 60.14 |  |
| VISC. CPS |  |  |  |
| BONDER 1000 CRS |  |  |  |
| CURE SCHEDULE | 20 min 80° C. | 100° C. 120° C. | 150° C. |
| FILM TH. MIL | 0.9–1.0 | 0.9–1.0 | 0.9–1.0 |
| HARDN. PENCIL | NO CURE 2B-B | H-2H | H-2H |
| KNOOP HARDNESS | 1.6 | 13.2 | 15.8 |
| IMPACT REVERSE IN. LB | 20–30 | >160 | 20–30 |
| FRONT IN. LB | >160 | >160 | 70–80 |

I claim:

1. A polymer blend comprising a mixture of:
   a. a hydroxyalkyl carbamate produced by reacting a cyclic carbonate with a diamine having the following structural formula:

$$H_2N-A-NH_2$$

wherein A is a branched alkylene moiety having attached thereto at least one alkyl group and having from 4 to 10 carbon atoms; and
   b. a crosslinking agent selected from the group consisting of methylol polyamine and polyisocyanate compound.

2. A polymer of:
   a. A hydroxyalkyl carbamate produced by reacting a cyclic carbonate with a diamine having the following structural formula:

$$H_2N-A-NH_2,$$

wherein A is a branched alkylene moiety having attached thereto at least one alkyl group and having from 4 to 10 carbon atoms, reacted with
   b. a compound selected from the group consisting of polyols, polycarboxylic acids, polycarboxylic acid esters and polycarboxylic anhydrides.

3. A polymer of claim 2, wherein said hydroxyalkyl carbamate is reacted with a compound selected from the group consisting of linear or branched polyester-based polyols and linear or branched polyether-based polyols.

4. A polymer of claim 2, wherein said hydroxyalkyl carbamate is reacted with a compound selected from the group consisting of polycarboxylic acids, polycarboxylic acid esters and anhydrides.

5. A polymer of claim 2, wherein said hydroxyalkyl carbamate is reacted with a compound selected from the group consisting of a di- and tri-carboxylic acids.

6. A polymer of:
   a. a hydroxyalkyl carbamate produced by reacting a cyclic carbonate with a diamine having the following structural formula:

$$H_2N-A-NH_2,$$

wherein A is a branched alkylene moiety having attached thereto at least one alkyl group and having from 4 to 10 carbon atoms, said polymer having terminal hydroxyl groups, reacted with
   b. a dimethyl ester of a dicarboxylic acid.

7. A process for the preparation of polyurethane polyols by the reaction of:
   A. bishydroxyalkyl carbamate, a reaction product of:
      (i) a diamine having the following structural formula:

$$H_2N-A-NH_2$$

wherein A is a branched cyclo alkylene group or a branched alkylene moiety having attached thereto at least one alkyl group and having 4 to 10 carbon atoms, with:
      (ii) a cyclic carbonate:

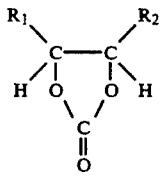

wherein $R_1$ is hydrogen, a $C_1$ to $C_{18}$ alkyl group, or a phenyl group and $R_2$ is hydrogen, a $C_1$ to $C_{18}$ alkyl group, phenyl group or $-CH_2-O-R_1$; with
   B. a compound selected from the group consisting of:
      (i) a lower alkyl ester of a dicarboxylic acid, wherein the lower alkyl has from 1 to 4 carbon atoms;
      (ii) a diol or polyol derived from alkylene oxides, having 2 to 6 carbon atoms and tetrahydrofuran; and
      (iii) polyesters of the reaction of a polyhydric alcohol and di-, tri-carboxylic acids.

8. A process for preparing a hydroxyalkyl carbamate by reacting a diamine having the structural formula:

$$H_2N-A-NH_2$$

wherein A is a branched alkylene moiety having attached thereto at least one alkyl group and having from 4 to 10 carbon atoms, and a cyclic carbonate:

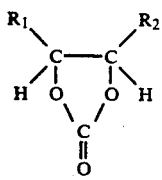
wherein $R_1$ is hydrogen, alkyl of $C_1$ to $C_{18}$, or phenyl and $R_2$ is hydrogen, alkyl of $C_1$ is hydrogen, alkyl of $C_1$ to $C_{18}$, phenyl or —$CH_2$—O—$R_1$ at a temperature between about 25° C. to about 150° C. and removing the excess water or cyclic carbonate by distillation.
9. A process according to claim 8 wherein the temperature of about 50° C. to 120° C.
* * * * *

UNITED STATES PATENT AND TRADEMARK OFFICE
CERTIFICATE OF CORRECTION

PATENT NO. : 5,134,205
DATED : July 28, 1992
INVENTOR(S) : Werner J. Blank

It is certified that error appears in the above-identified patent and that said Letters Patent is hereby corrected as shown below:

Column 3, lines 37-38, "dipropyleneglycol" should be -- dipropylene glycol --.

Column 3, line 54," polyestes" should be -- polyesters --.

Column 4, line 19, "com-pounds" should be -- compounds --.

Column 4, line 63, "usign" should be -- using --.

Column 5, lines 22-23, "hydroxylalkyl" should be -- hydroxyalkyl --.

Column 6, line 7, "0.8 MEQ/g" should be -- 0.08 MEQ/g --.

Column 7, line 1, "propylene car-bonate" should be -- propylene carbonate --.

Column 8, line 3, "called" should be -- cooled --.

UNITED STATES PATENT AND TRADEMARK OFFICE
CERTIFICATE OF CORRECTION

PATENT NO. : 5,134,205
DATED : July 28, 1992
INVENTOR(S) : Werner J. Blank

It is certified that error appears in the above-identified patent and that said Letters Patent is hereby corrected as shown below:

Column 8, line 41, "MEW" should be -- MEQ --.

Column 10, line 56, "adesin" should be -- adhesion --.

Column 11, line 16, "1,6-hexaediamine" should be -- 1,6-hexanediamine --.

Column 11, line 28, "isocyantate" should be -- isocyanate --.

Column 11, line 29, "N-399" should be -- N-3990 --.

Column 11, line 29, "formula-tion" should be -- formulation --.

Column 11, line 38, "A0608S" should be -- AU608S --.

Column 13, line 17, under CURE SCHEDULE, "100°C." should be deleted.

Signed and Sealed this

Twenty-third Day of November, 1993

Attest:

BRUCE LEHMAN

Attesting Officer

Commissioner of Patents and Trademarks